United States Patent
Lacombe et al.

(10) Patent No.: US 7,513,619 B2
(45) Date of Patent: Apr. 7, 2009

(54) HIGH RESOLUTION LATERIAL AND AXIAL TOMOGRAPHY

(75) Inventors: François Lacombe, Chaville (FR); David Lafaille, Meudon (FR); Marie Glanc, Meudon (FR); Eric Gendron, Meudon (FR)

(73) Assignees: Centre National de la Recherche Scientifique, Paris (FR); Observatoire de Paris, Paris (FR); Mauna Kea Technologies, Paris (FR)

( * ) Notice: Subject to any disclaimer, the term of this patent is extended or adjusted under 35 U.S.C. 154(b) by 412 days.

(21) Appl. No.: 10/586,716

(22) PCT Filed: Jan. 21, 2005

(86) PCT No.: PCT/FR2005/000132

§ 371 (c)(1),
(2), (4) Date: Jul. 20, 2006

(87) PCT Pub. No.: WO2005/080911

PCT Pub. Date: Sep. 1, 2005

(65) Prior Publication Data

US 2008/0231807 A1    Sep. 25, 2008

(30) Foreign Application Priority Data

Jan. 22, 2004  (FR) ................... 04 00582

(51) Int. Cl.
*A61B 3/10* (2006.01)
*G01B 11/02* (2006.01)

(52) U.S. Cl. .............. 351/205; 351/221; 351/246; 356/497; 378/21

(58) Field of Classification Search ........... 351/211, 351/221, 246
See application file for complete search history.

(56) References Cited

U.S. PATENT DOCUMENTS

| 6,588,900 | B1 | 7/2003 | Le Gargasson et al. |
| 6,735,463 | B2* | 5/2004 | Izatt et al. ............ 600/476 |
| 7,364,296 | B2* | 4/2008 | Miller et al. .......... 351/221 |
| 2006/0176448 | A1* | 8/2006 | Van de Velde ......... 351/221 |
| 2008/0013078 | A1* | 1/2008 | Podoleanu et al. ....... 356/73 |

FOREIGN PATENT DOCUMENTS

| WO | WO 03/020121 | 3/2003 |
| WO | WO 03/105678 A2 | 12/2003 |
| WO | WO 03/105678 A3 | 12/2003 |

* cited by examiner

*Primary Examiner*—Jordan M. Schwartz
(74) *Attorney, Agent, or Firm*—Greer, Burns & Crain, Ltd.

(57) ABSTRACT

An in-vivo high resolution lateral and axial tomography system of the retina, is provided, including a Michelson interferometer, generating a tomographical image by full field OCT interference with Z sweeping, adaptive optical correction apparatus, correcting the wave fronts coming from and going to the eye, including a reference source, a deformable mirror and wave surface analysis apparatus, detection apparatus producing an image from an interferometric measurement using the OCT principle and apparatus for focussing the wave surface analyser. The apparatus for focussing are embodied and controlled, synchronously with the Z sweeping to force the deformable mirror to adopt an additional curvature, such as to combine the input light source and detection apparatus at a given depth in the retina.

34 Claims, 3 Drawing Sheets

HIGH RESOLUTION LATERAL AND AXIAL TOMOGRAPHY

This invention relates to an in vivo tomography system with high lateral and axial resolution of the human retina. It also relates to a method implemented in this system.

BACKGROUND OF THE INVENTION

In order to carry out high axial resolution tomography of a biological tissue, there already exists the well known technique of tomography by interferometry with a short coherence length (OCT, for Optical Coherence Tomography). For example, the work by M. E. Brezinski and J. G. Fujimoto can be mentioned, in particular in the article "Optical Coherence Tomography in Non Transparent Tissue">>, IEEE J Sel Topics in Quant Elect, 5: 1185, 1999. This technique relies on a device of the Michelson interferometer type, which consists of making two light beams originating from a single source interfere, one of which is reflected on a reference mirror and the other on a sample to be investigated. The lighting of the device by a source of short coherence length makes it possible to only obtain interferences with which the light returned by a thickness of the sample produces equality of the optical paths in the two arms, at best half the temporal coherence length in the medium.

When the sample to be investigated is arranged in an aberrant medium, or after aberrant optics, such as that of the eye for example, outward and return beams to and from the sample are affected by geometric aberrations. This results in two significant consequences:

Each point of the source of the device, extended in the case of a full-field system, sees its image in the volume of the sample degraded by geometric aberrations: the illuminated area is much greater, or even multiple if "speckles" flash on the image. This calibration effect in the sample is manifested by a spatial mix of the information fed back, and thus by a loss of spatial resolution. It also manifests itself by a lowering of the lighting level, and thus by a lowering of sensitivity.

On the return path, each point of the sample produces a wavefront, which altered again by geometric aberrations, can only interfere partially with the return beam of the reference arm, by the absence of mutual coherence of the wavefronts. The expected contrast of the interference fringes is reduced by a factor $e^{-\sigma^2}$, where $\sigma^2$ is the spatial variance of the phase of the disturbed wave front. This phenomenon is well known by interferometry astronomers, who can only design interferometers with a number of telescopes when the pupils of the latter are coherent, either naturally with a large wavelength, or after restoration by an adaptive optical system. In the case of an OCT system, the loss of contrast is manifested directly by a loss of sensitivity.

Therefore, an input source point is no longer conjugated at a single point of the sample, even close to the diffraction, and a fortiori even less with the detector arranged at the output, although this is still the case for the beam circulating on the reference arm.

These limitations due to geometric aberrations are an additional difficulty intrinsic to the OCT technique: that is a change of observation distance by movement of a reference mirror must correspond to a change of focussing distance (without additional variation of the path difference) in the sample, without which there will again be loss of contrast.

The result of this is that a tomography system used in an aberrant medium sees its spatial resolution and its sensitivity reduced simultaneously owing to geometric aberrations and focussing changes. An OCT tomography system can, by coupling with an adaptive optical method (OA), see its sensitivity and its spatial resolution improved when it is used in media or with optics generating significant geometric aberrations, a fortiori when these aberrations vary over time. Adaptive optics is a technique for restoring wavefronts, which relies on a measurement of the disturbances of the wavefront and on a closed loop correction of this wavefront via a corrective system. There are various ways to measure a wavefront, and therefore different types of analyser. The analyser of the Shack-Hartmann type is the most used, as is illustrated by the documents U.S. Pat. Nos. 6,299,311 and 5,777,719. Applied to the eye, the measurement of the wavefront is carried out on the beam returning from a light spot imaged on the retina. There are also different types of corrective system, deformable mirrors being the most common.

An OCT+OA coupling has already been envisaged as a three-dimensional (3D) imaging solution for biological media. However, the sensitivity levels currently obtained with systems implementing this coupling are clearly insufficient to envisage an in vivo tomography system for the examination of a human retina, for which the measurement conditions are very difficult given ocular movements.

SUMMARY OF THE INVENTION

The purpose of the invention is to propose a tomography system with high axial and lateral resolution of the human retina, implementing an OCT+OA coupling and enabling in vivo tomography.

This objective is achieved with an in vivo tomography system with high axial and lateral resolution of the human retina, comprising:

a Michelson interferometer, producing a full-field tomography setup by interference with short coherence length (OCT) with a Z scanning, an input light source arranged in an input arm of the interferometer, adaptive optical means, arranged between the interferometer and an eye to be examined, designed to correct wavefronts originating from the eye and directed to the eye, comprising a reference source, a deformable mirror and means of analysing the wave surface, means of detection, arranged in an imaging arm of the interferometer, designed to produce an image from an interferometric measurement according to the OCT principle, and means of adjusting the focussing of the means of analysis of the wave surface.

According to the invention, the means of adjusting the focussing are arranged to force the deformable mirror to adopt an additional curvature, so as to conjugate the input light source and the means of detection with a point at a predetermined depth in the retina, said means of adjustment being controlled in synchronism with the Z scanning of the OCT tomography set up.

In order to restore the resolution and the contrast, it is important for the corrective optics to be capable of correcting, in the arm to the sample, both incident wavefronts and reflected wavefronts. The adaptive optics should therefore be found entirely in the arm of the Michelson interferometer leading to the sample, together with its reference source and its analyser.

Under these conditions, the corrective optics can, from wavefront measurements made by the analyser, compensate for the perturbations which the wavefront will encounter as it passes through the optics and the medium surrounding the sample. A corrected image of each point of the source and thus close to the diffraction limit, is produced in the depth of the sample. The fogging of the spatial information disappears and the light concentration increases.

On return, the same correction is still valid in order to compensate for the geometric aberrations caused by passing through the medium and the optics. An image, itself also close to the diffraction, is then available and capable of interfering with the maximum contrast with its reference arm homologue.

In addition, the measurement of the contrast of the fringes without modulation by the Wollaston method guarantees the interferometric coherence of the four two-dimensional (2D) interferograms required to measure the 2D retina reflectance card for a given depth. A second purpose of the invention aims at optimising the sensitivity of the OCT device. The geometric aberrations encountered in the eye on the "outward" path considerably degrade the Michelson Interferometer Source/Retina conjugation. Consequently, the lateral resolution of the lighting is greatly reduced. These aberrations increase very quickly with the diameter of the pupil used. Conventionally, reduction in the diameter of the input beam makes it possible to limit the effects of these aberrations. However, the diffraction limit increases and the maximum lateral resolution also decreases.

Moreover, the geometric aberrations encountered in the eye on the "return" path considerably degrade the Retina/Detector conjugation. Consequently, the lateral resolution of the restored image is greatly reduced. Here also, reduction in the diameter of the output beam makes it possible to limit the effects of these aberrations. However, the diffraction limit again increases in this case and the maximum lateral resolution decreases. Moreover, reduction in the diameter of the beam is accompanied by a reduction in the collecting surface at the output of the eye and therefore the sensitivity of the examination.

Furthermore, the geometric aberrations encountered in the eye on the "outward and return" path considerably degrade the conjugation between the images of the source seen through the two arms of the Michelson interferometer. Consequently, the interferometric contrast is greatly reduced. This effect appears only when a pupil with too large a diameter is used as, in the opposite case, reduction in the diameter makes it possible to limit aberrations.

These drawbacks are remedied with an in vivo tomography system according to the invention, comprising means for increasing the interferometric contrast by compensation of the geometric aberrations of the eye, in the form of adaptive optical means inserted into the interferometer measurement arm, and means to compensate for the effects of birefringence of the cornea by the introduction of a compensator in front of the eye.

The adaptive optical means, advantageously produced in the form of a deformable mirror, are installed between the Michelson interferometer and the eye. They compensate for the aberrations which the beam is subject to when leaving the eye, and pre-compensate at the same time for the aberrations which the outward beam is subject to on entering the eye. The use of adaptive optical techniques in ophthalmoscopes is already known from the prior art, in particular from the document EP 1 164 921 B1 which discloses an adaptive optical system implemented in a scanning laser ophthalmoscope (SLO).

The lateral resolution of the lighting is thus restored. The lateral resolution of the examination is restored. The interferometric contrast is optimum, even with the pupil fully open.

The control of the adaptive optical means is established on the basis of wavefront measurements carried out downstream of said adaptive optical means (in the return direction) on the image of a reference point source installed on the retina. This point source is obtained by the introduction of an additional light beam, independent of the measurement beam, focussed on the retina. Depending on the desired level of optimisation, the "outward" reference beam can or cannot pass through the adaptive optical means and benefit from the adaptive correction.

The OCT measurement assumes the equality of the optical paths between the two arms of the Michelson interferometer, at whithin the coherence length of the source. It also assumes an optimum adjustment on the depth which corresponds to this equality.

Conventionally, the limitation on the diameter of the beam confers on the eye a very large depth of field, which dispenses with any readjustment.

When the system is used at full opening (typically F/3), the field depth reduces rapidly, typically 30 μm. The Z scanning of the OCT can produce a rapid exit from this interval, above which the interferometric contrast decreases. This can be considered as an aberration effect of pure defocus.

This problem may be remedied by providing the wave surface analyser with a device capable of adjusting its own focussing, for example with a mechanical adjustment. An arbitrary modification of this focussing, forces, via the adaptive optical loop, the deformable mirror to adopt an additional curvature, conjugating input source and detector with a point more or less deep in the retina. The control of this focussing should be synchronized with Z scanning of the OCT.

It is also possible to control the analyser in order to force it to work in an defocussed mode. Some advanced analysers, for example models from the company. Imagine Optic, are actually capable of working in defocussed mode with good results.

An alternative solution to an actual defocussing of the analyser may consist of adding a pure focus term into the mirror control, regardless of the analyser measurement. This artifice is commonly used in adaptive optics. With an analyser of the Shack-Hartmann type, one just has to modify the table termed "reference slopes" which forces the system to converge towards an arbitrarily modified control.

Another purpose of the invention aims at optimising the photometric yield of the Michelson interferometer implemented in the in vivo tomography system according to the invention. This objective is achieved with an in vivo tomography system according to the invention operating in light polarized linearly and in which the polarization is switched between outward and return in the arms with a quarter-wave plate.

The use of polarized light makes it possible to:
limit the degradation of the interferometric contrast by the effects of birefringence of the eye. In fact, any rotation or change to the polarization of the light on its passage into the eye is accompanied by a loss of interferometric contrast by the simple loss of conservation of the amplitude of the field in the initial direction of polarization;
optimize the transmission on return from the eye. In fact, the use of a polarizing separator cube as a separating guide plate and the rotation of the polarizations in the two arms by an angle of 90 degrees between outward and return with a quarter-wave plate makes it possible to collect at the output from the system all the energy returned by the eye and not half, as is conventionally the case with a Michelson interferometer.

In one particular form of the invention, aimed at filtering at best any parasitic reflection of instrumental origin, the quarter-wave plate is placed as close as possible to the eye, but before the birefringence compensator.

One may advantageously contribute to filtering at best the corneal reflection in the in vivo tomography system according to the invention, by using a Gauss setup, by which the addition of a field diaphragm stops the essential part of the flux reflected by the cornea.

An optimisation of the wavefront measurement may be advantageously obtained by installing the reference source upstream of the adaptive optical compensator means.

In order not to defocus the reference source when the adaptive optical compensator means, represented for example by a deformable mirror, are defocussed in order to tune the adjustment to a given depth, means may also be provided for tuning this adjustment through a response from the adaptive optical compensator means to an overall defocussing of the source+analyser assembly.

The retinal image of the reference source thus remains unchanged although the compensator means conjugate a different plane from the retina to the output camera.

With the aim of optimising the fixation of the subject, an active target pattern may advantageously be provided.

In order to guarantee the interferometric stability of the measurements, despite the adaptive character of the wavefront corrections, means may also be provided to freeze the form of the adaptive optical compensator means, for example the deformable mirror, during the exposure period.

According to another aspect of the invention, an in vivo tomography method is proposed with high axial and lateral resolution of the human retina, comprising:
  a full-field tomography by interference at a short coherence length (OCT) with a Z scanning, using an input light source,
  a production of an image of the retina by detection means, from an interferometric measurement according to the OCT principle,
  a correction of the wavefronts originating from the eye and reaching the eye, by adaptive optical means, arranged between the interferometer and the eye, comprising an analysis of the wave surface on the retina, and
  an adjustment of the focussing of the wave surface analysis,
characterized in that the focussing adjustment is carried out so as to conjugate the input light source and the detection means with a point of predetermined depth in the retina, in synchronism with the Z scanning of the OCT tomography.

BRIEF DESCRIPTION OF THE DRAWINGS

Other advantages and characteristics of the invention will become apparent on examination of the detailed description of an embodiment which is in no way limitative, and the attached diagrams, in which.

DETAILED DESCRIPTION OF THE PREFERRED EMBODIMENTS

Figure 1:
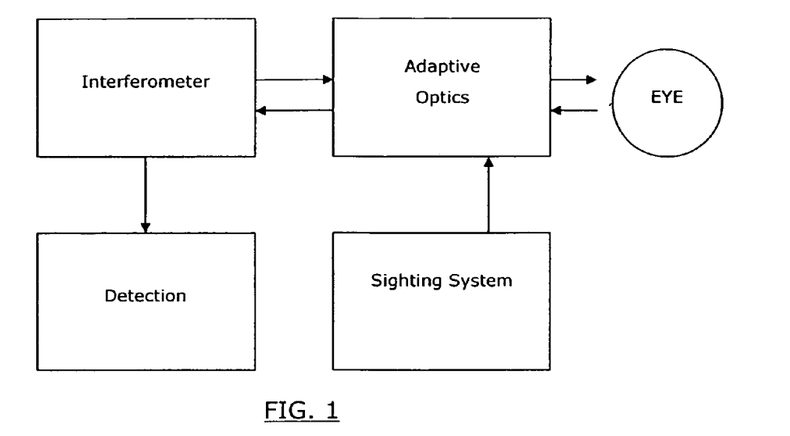
FIG. 1 is a block diagram of an in vivo tomography system according to the invention.

An in vivo tomography system according to the invention comprises, with reference to FIG. 1:
  a Michelson interferometer, producing a full-field OCT setup,
  an adaptive optical device, arranged between the interferometer and an eye to be examined, producing correction of the wavefronts originating from the eye as well as those reaching the eye,
  a detection device, arranged downstream of the interferometer, making it possible, without synchronous modulation or detection, to carry out the interferometric measurement according to the OCT principle, and
  a sighting system, to guide the sight of the patient while at the same time ensuring his visual comfort and optimising his fixation performances.

Figure 2:
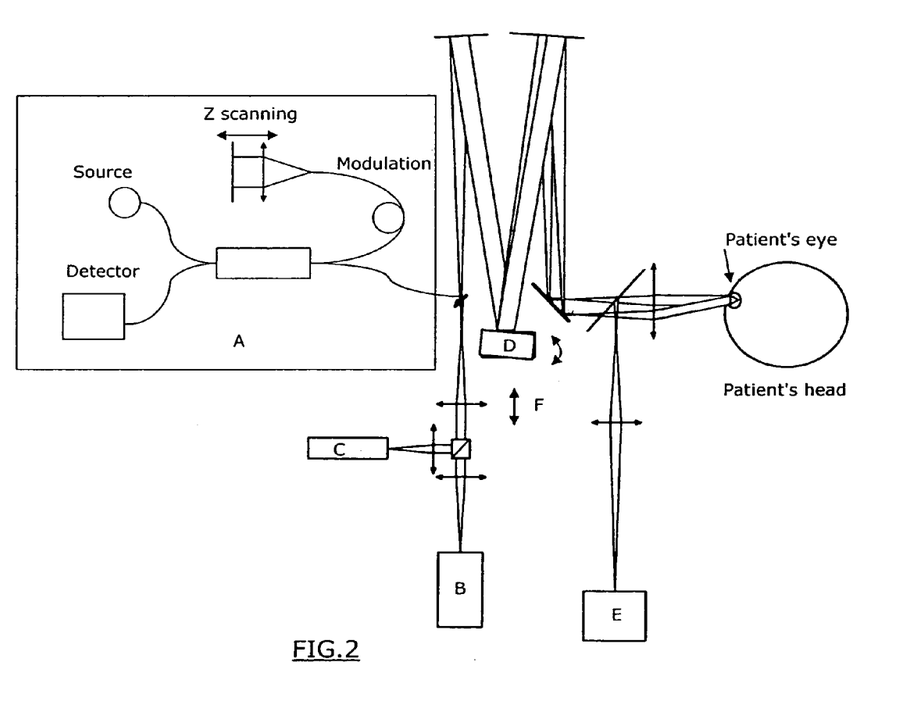
FIG. 2 illustrates diagrammatically the theoretical structure of an in vivo tomography system according to the invention.

Firstly, the principle of OCT+OA coupling used in a first embodiment of an in vivo tomography system according to the invention will be described with reference to FIG. 2. This system comprises an OCT tomography system A, a wavefront analyser B, a reference source C, a deformable mirror D also ensuring the function of scanning the eye in one or two spatial dimensions, a sighting system E and a lens F for controlling the focussing.

The OCT tomography system A, of conventional structure, comprises a source, a detector, a Z scanning device and a modulation.

A translation of the lens F may impose, via the reaction from the adaptive system, a particular control may, in combination with the movement of the reference mirror, observe each layer of the sample with optimum contrast.

Figure 3:
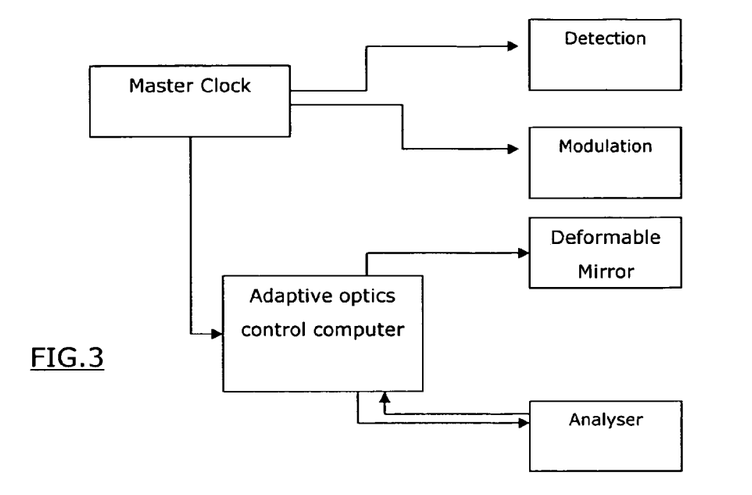
FIG. 3 is a block diagram of a device for controlling an in vivo tomography system according to the invention.

This arrangement of the complete adaptive setup in the arm of the Michelson interferometer makes correction of the wavefront possible. The OCT systems used currently on biological tissues such as an eye extract a low interferometric signal available from the incoherent base, using synchronous detection techniques associated with a modulation of the optical path, most often by a change to the length of the fibre on the reference arm. This modulation must in this case be synchronized with the wavefronts in order that no additional path difference of 'adaptive' origin can disturb the interferometric measurement. Beyond this, i.e. over time intervals longer than the modulation/demodulation period of the system, the path difference must also be maintained constant at whithin half the coherence length, as it is in fine the latter which fixes the resolution in depth of the system. A control device, as illustrated diagrammatically in FIG. 3, is programmed to ensure this control of the path difference. This control device may comprise a master clock delivering a clock signal to the detection unit, to a modulation unit and to a computer controlling the adaptive optics, which drives a deformable mirror and an analyser.

A practical example of an in vivo tomography system according to the invention will now be described, by reference to FIG. 4. The interferometer, of the Michelson type, comprises a measurement arm designed to illuminate the eye and collect the returned light, and a reference arm designed to illuminate a moving mirror enabling in depth exploration of the retinal tissue.

The interferometer is used with light polarized rectilinearly and perpendicularly in the two arms. The light source S is a diode with a short temporal coherence length (for example, 12 µm), the spectrum of which is centred on 780 nm. In theory, it confers on the in vivo tomography an axial resolution equal to half the coherence length divided by the refractive index of the medium.

This light source S may be pulsed. In this case, it is then synchronised with the shot of the image and the adaptive correction. The beam is limited by a field diaphragm corresponding to 1 degree in the field of view of the eye (300 µm on the retina) and a pupil diaphragm corresponding to an opening of 7 mm on a dilated eye.

An input polarizer P provides optimal balancing of the flux injected into the two arms of the interferometer.

The two arms have a configuration termed Gauss, afocal, which enables the conjugation of the pupils on the one hand, and the materialisation of an intermediate image of the field where a diaphragm blocks a large part of the corneal reflection, on the other hand. Quarter-wave plates ensure by the rotation of polarization of the sole light returned by the eye, and the moving mirror, an effective filtering of parasitic reflections in the in vivo tomography system according to the invention.

In order to maintain the equality of the optical paths in the two arms, with the same conjugation of the pupils and the field, the reference arm is similar to the measurement arm but with a static optic.

The detection path of the in vivo tomography system according to the invention will now be described. The two beams on the output arm are still polarized perpendicularly, and they interfere only if they are projected on a common direction. A Wollaston W prism has the function of simultaneously projecting the two radiations on two perpendicular analysis directions. A simultaneous measurement of the intensity may then be made after interference in two interference states in opposition, without synchronous modulation or detection, on a single two-dimensional detector. The addition of a quarter-wave plate, after division of the beam, makes it possible to access two additional measurements, thus removing any ambiguity between the amplitude and phase of the fringes. A half-wave plate at the input to the detection path or before the Wollaston prism enables suitable orientation of the incident polarizations.

The Wollaston prism is placed in a pupil plane, hence conjugated with the separator cube of the Michelson interferometer. The separation angle of the Wollaston prism is chosen as a function of the field to be observed. The focal length of the final objective determines the sampling interval of the four images.

The detector is of the CCD type, with an image rate of more than 30 images per second. This detector is associated with a dedicated computer (not shown) in which the digital processing of the images is carried out: extraction of the four measurements, calibration, calculation of the amplitude of the fringes.

The adaptive correction of the wavefronts is carried out upstream of the interferometer and thus in the measurement arm. Each point of the source S thus sees its image on the retina corrected of aberrations, and the return image is also corrected. The amplitude of the fringes is thus maximum.

The adaptive optics sub-assembly comprises a deformable mirror MD. Measurement of the wavefront is carried out by an analyser SH of the Shack-Hartmann type on the return beam of a light spot itself imaged on the retina via the deformable mirror MD. The analysis wavelength is 820 nm. Illumination is continuous and provided by a temporally incoherent superluminescent diode SLD. The dimensioning of the analyser corresponds to an optimisation between photometric sensitivity and wavefront sampling. The control refreshment frequency of the deformable mirror MD may reach 150 Hz. A dedicated computer (not shown) manages the adaptive optical loop. The control is, however, synchronised in order to freeze the shape of the mirror during the interferometer measurement.

An appropriate control on the focussing of the analysis path, using a lens LA2, enables to adapt the focussing distance to the layer selected by the interferometer. This arrangement is essential for maintaining an optimum contrast at any depth.

The deformable mirror MD is conjugated with the pupil of the system and of the eye. The field of the system is defined by the system input field diaphragm DCM. It is chosen equal to 1 degree, i.e. less than that of the isoplanetism field of the eye, which guarantees the validity of the adaptive correction in the field of the only wave front measurement made from the spot, at the centre of the field. Moreover, the rotation of the deformable mirror MD makes it possible to choose the angle of arrival of the beam in the eye and thus the portion of the retina studied.

The addition of corrective lenses to the subject's view, thus low orders of geometric aberrations such as focus or astigmatism, just in front of the eye, makes it possible to loosen the requirements on the travel of the deformable mirror MD, and also guarantee an improved sighting. An adaptive corrective system by transmission can be used in preference to fixed lens for an optimum correction.

A collaborative or active sighting device is installed upstream of the assembly. This sighting system, which comprises an active target pattern MAM, presents to the subject the image of a light spot, deviating periodically from the sought sighting axis. The patient is then invited to follow all the movements of this image. Each time that the image returns to the axis, and after an adjustable latency time, a series of interferometric measurements is carried out. The periodic movement of the view makes it possible to obtain from the patient an improved fixation capacity when he aims at the desired axis. The amplitude and the frequency are adaptable to the subject and to the measurements undertaken. For reasons of convenience, the target pattern may be produced with a simple office computer on which a light spot is displayed and moved. The active target pattern MAM, the adaptive optics, the source S and the image shot are synchronized.

An embodiment of each of the sub-assemblies of an in vivo tomography system according to the invention will now be described, with reference to FIG. 4.

The input arm comprises successively the source S, typically an electroluminescent diode with a power of 30 mW with a wavelength of 780 nm, the Hitachi model HE7601SG, a condenser LE1 produced in the form of an objective of a microscope, a field diaphragm DE1, and a collimator LE2.

The reference arm comprises successively a separator CPR produced in the form of a wideband polarizing cube, a first Gauss lens LR1 of focal length 125 mm, a first mirror MR1 for returning the beams, a first parabolic mirror MPR1 for the parabolic return of the beams, a second mirror MR2 for returning the beams, a second parabolic mirror MPR2 for the parabolic return of the beams, a second Gauss lens LR2, a quarter-wave plate QOR carrying out a polarization rotation function, a third lens LR3 for focussing and a final spherical mirror MR3 with curvature centred on the centre of the lens LR3. This mirror MR3 ensures both the reference retina function of the interferometer and the function of reconjugating the pupil on return.

The measurement arm comprises a first Gauss lens LM1, a field diaphragm DCM, a beam splitter SFP1, a second Gauss lens LM2, a separator CPA in the form of a wideband polarizing cube, a focussing lens LA3, a Shack-Hartmann analyser SH, a focussing lens LA4, an analysis source SLD with a wavelength of 830 nm, a first parabolic mirror MPM1 for the parabolic return of the beams, a deformable mirror MD comprising 31 electrodes, a second parabolic mirror MPM2 for the parabolic return of the beams, a mirror MM1 for returning the beams, a pellicule beam splitter SFP2, a Gauss lens LM2', a quarter-wave plate QOM for rotation of polarization, an adaptive lens LAM, a focussing lens LM2 and an active target pattern MAM.

The imaging arm comprises a half-wave plate DOP/M provided to carry out a switching of polarizations, a non-polarizing separator cube BSP/M, a mirror MP/M1 for returning the beams, a quarter-wave plate QOP/M for creating a differential delay function of the polarizations on one of the beams, a mirror MP/M2 for returning the beams, a mirror MP/M3, a collimation lens LP/M2, a Wollaston prism W for projecting of polarizations, an objective lens LP/M3 and a detector CCD. The quarter-wave plate may advantageously be placed just before the Wollaston prism, in which case the polarizations travel in the measurement arm with the orientation that they have in the interferometer (on return). The measurement arm quarter-wave plate must therefore be oriented accordingly.

Figure 4:
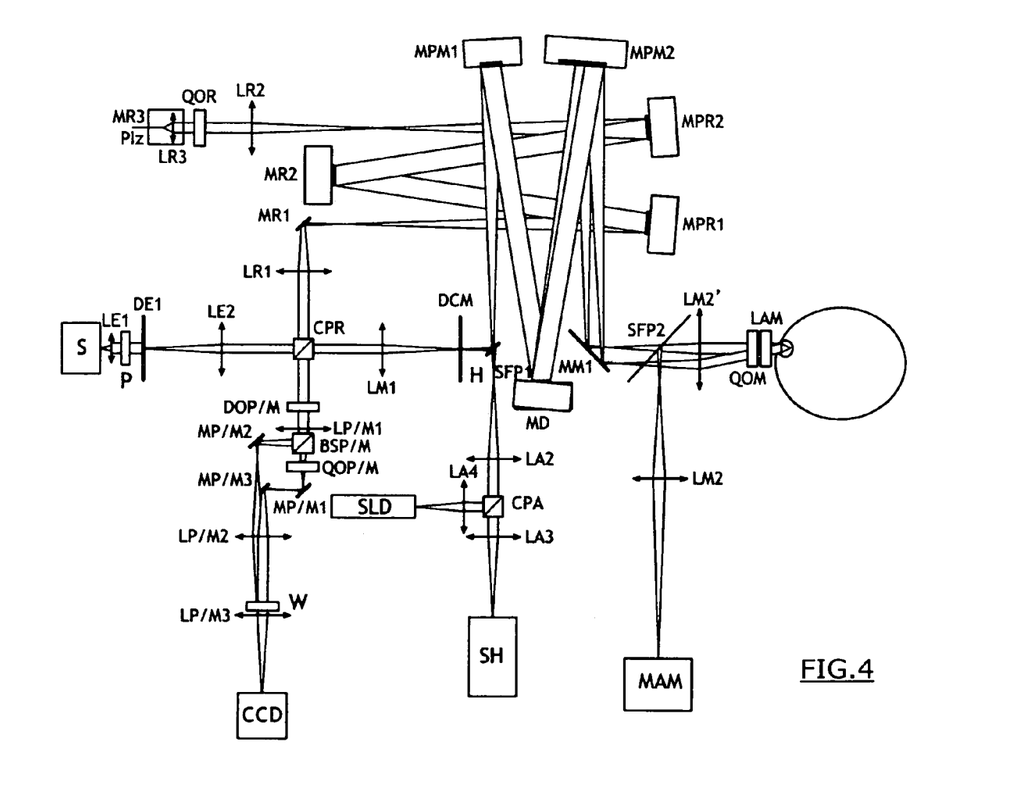
FIG. 4 is a diagram of a practical embodiment of an in vivo tomography system according to the invention.

In the practical embodiment illustrated by FIG. 4, the in vivo tomography system according to the invention is relatively compact at less than 1.2 m sideways. A significant part of the size constraint comes from the diameter of the deformable mirror MD which fixes in part the focal length of the off-axis parabolas. The use of micro-mirrors would obviously reduce all the dimensions of the system.

The detection system, with its division into two beams, is produced here with discrete components. The production and use of integrated components combining the functions of separation, folding or even delaying the beams may be envisaged.

The technical performances of the in vivo tomography system according to the invention will now be explained, in its practical configuration represented in FIG. 4. With each exposure, a full-field image of the retina is produced, with a diameter of 1 degree. The image is corrected for geometric aberrations, and thus close to the diffraction limit (1.8 microns at 780 nm wavelength). The simultaneous character, as full field, of the measurements at any point confers on the image maximum mapping accuracy. Moreover, the simultaneous character of the interferometric measurement guarantees the conservation of the resolution in depth: 4.5 microns with a source of 12 µm coherence length. Thus the conjugated use of a full-field interferometric technique, of an upstream adaptive optics, and of a simultaneous detection without modulation, makes it possible to obtain three-dimensional images in vivo. Furthermore, the active target pattern optimises the operational performance of the system.

The full-field character of the OCT device used in the in vivo tomography system according to the invention provides a gain in sensitivity which is multiplex in nature, namely a gain obtained by paralleling the integration of the light flux from the different points of the field, by comparison to any scanning technique. The use of an adaptive optics guarantees not only the restoration of the image quality but also of the interferometric contrast. As regards analysis of the wavefront, it will be noted that the installation of the reference source upstream of the deformable mirror guarantees an optimum quality of the aberration measurements, as the reference image materialised in the eye benefits from adaptive correction. This optimisation remains true whatever the focussing, the source being upstream of the adjustment control system. Finally, the use of a polarizing cube in this case makes it possible to use all the photons originating from the eye. Measurement of the wavefront is therefore made under the best conditions.

The instantaneous field accessible to the system, thus on one exposure, is approximately one degree, i.e. 300 µm on the retina. If the in depth scanning device is used between each shot, up to 30 tissue planes can be examined in 1 second. If the patient can maintain his fixation for 2 seconds, and if the distance between the planes is chosen to equal 2 µm, for example, a volume of 300×300×120 µm of retinal tissue can thus be observed, with a resolution of 1.8×1.8×4.5 microns.

The option of rotation of the deformable mirror also brings to the in vivo tomography system according to the invention the ability to explore a broader field, over several degrees and thus to examine the more peripheral regions of the foveolar zone.

As regards analysis of the wavefront, it will be noted that the installation of the reference source SLD upstream of the deformable mirror MD affords optimum quality of aberration measurements and thus their compensation, as the reference image materialised in the eye benefits in this case from adaptive correction. This optimisation remains true whatever the focussing, the source SLD being upstream of the adjustment control system. Finally, the use of a polarizing cube CPA (FIG. 4) in this case makes it possible to use all the photons originating from the eye. Measurement of the wavefront is therefore made under good conditions.

However, it should be noted that a very precise lateral optical conjugation is required between the reference source SLD and the input of the analyser SH. In the case where this conjugation is insufficient, an attempt at compensation of a conjugation error by the adaptive optical loop can lead to a divergence of the servo-control.

Figure 5:
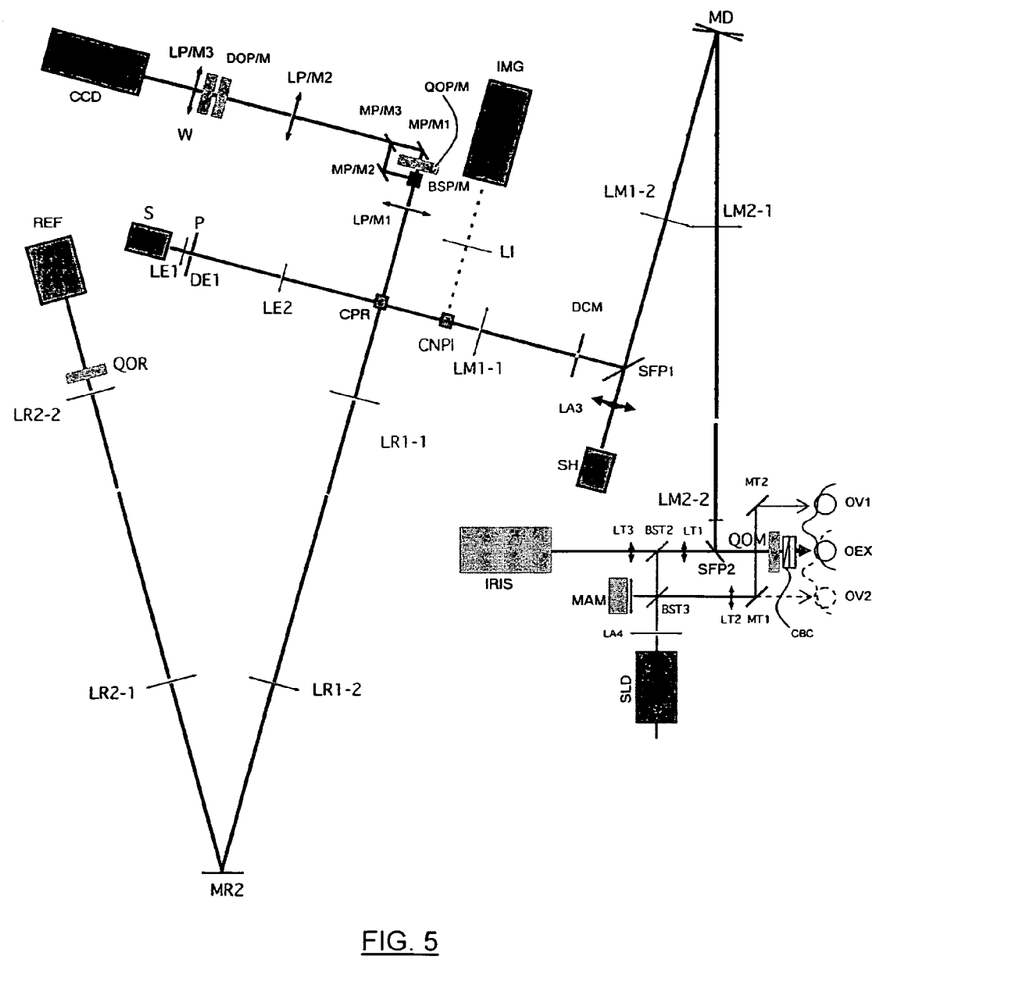
FIG. 5 is a diagram of another embodiment of an in vivo tomography system according to the invention.

A variant of the invention, illustrated in FIG. 5, enables greater simplicity in the system, by reducing this risk of instability in the adaptive optical loop. In this variant, the reference source SLD is positioned closer to the eye in the optical path, in particular after the adaptive optics (outwards) and, for example, before a birefringence compensator, such as a Soleil-Babinet compensator CBC, or just before the eye. In the absence of benefiting from an optimum image spot at the base of the eye, the system then benefits from operational stability.

The deformable mirror used in the adaptive optics may be, for example, a 50 mm diameter mirror with 31 elements from the CILAS company. However, the performances and/or compactness of the device can be improved by using a higher performance and/or more compact model such as the deformable 15 mm diameter mirror with 52 elements developed at the Astrophysics Laboratory of the Grenoble Observatory, in particular due to its compactness and a larger travel in the adaptation movements.

In the example illustrated in FIG. 5, the folding reflectors of the measurement arms MPM1, MPM2 and those of the reference arms MPR1, MPR2 have been eliminated. The optical path of the measurement arm comprises a doublet of two lenses LM1-1 and LM2-2 on one side of the deformable mirror MD, and another doublet of two lenses LM2-1 and LM2-2 on the other side of this deformable mirror. Similarly, the optical path of the reference arm comprises a doublet of two lenses LR1-1 and LR2-2 on one side of the reference mirror MR, and another doublet of two lenses LR2-1 and LR2-2 on the other side of this deformable mirror.

The use of lenses rather than mirrors may be more economical and enable better performance, in particular due to the cost and the optical aberrations of this type of mirror, which are typically off-axis parabolic mirrors.

The combination of such an on axis setup, with a smaller deformable mirror, make it possible to obtain a system which performs better, is simpler, or is more economic, while retaining a limited size.

As illustrated in FIG. 5, the system may also comprise conventional imaging means, such as a camera IMG, capable of combining interferometric measurements with a simple imaging of the zones examined, for example to facilitate the exploration and selection of the zones to be examined.

Arranged directly at the output (on the return) of the measurement arm, and therefore just before the polarizing cube CPR of the interferometer, a second polarizing cube CNPI may deflect the return beam to an imaging camera IMG having its own means LI of focussing the image. On this path, a direct image of the sighted retinal zone will be observable. In particular the measurement arm and this additional path may be arranged such that a wider field of observation is provided than with the interferometric mode, the field of which is -limited, in particular by the interferometric contrast measurement technique in itself.

Due to its low coherence length, the input source S has a spectrum of the polychromatic type. In a typical OCT set up, this spectrum is in general relatively narrow, for example with a width of approximately 50 nanometers, but not necessarily negligible.

This polychromatic spectrum can cause a deterioration in performance, in particular by leading to a dispersion of the path differences due to the dispersive characteristics of the ocular environment, which leads to a deterioration in the axial resolution of the device. In order to avoid or limit these deteriorations, the system may comprise compensation means situated in the reference arm.

Moreover, the dispersive character of ocular media is also manifested by a variation in the focus of the eye with the wavelength, also leading to a deterioration in axial resolution. In order to avoid or limit these deteriorations, the system may therefore comprise compensation means situated for example in the measurement arm. In particular, these means may compensate for a focal chromatism which represents approximately 400 micrometers between the red and the blue, for example by replacing the collimator LM2-2 situated just in front of the eye by a doublet with chromatism chosen deliberately opposite to that of the eye. These means may also compensate for optical path differences due to chromatic dispersion, for example by inserting a water tank into the reference arm of a size dependent and/or controllable according to the size or to the characteristics of the eye to be examined. Such a tank may have a size of the order of 24 mm, the average length of a human eye.

With a 12 micrometers coherence length source and spectrum width of 50 nanometers, the use of these compensation means may enable improvement in the axial resolution by changing it from a value of approximately 6 micrometers to a value of approximately 4 micrometers.

In order to improve performance, in particular in terms of axial resolution, the system may also use as input source for the interferometer a polychromatic illumination with a wider spectrum, for example white light. In this case, the improvement in performance provided by these means will be much more significant.

In the example illustrated in FIG. 5, the system is arranged so that the target of the active target pattern MAM is visible by both eyes OD1 and OG1 of the subject to be examined. A sighting with both eyes may actually improve the fixation or stability performances and facilitate the examination. In this example, the image of the target pattern is introduced into the optical path between the reference source SLD and the eye examined by a separator BST3.

This separator may be chosen dichroic for reflecting 50% of all the light coming from the target pattern MAM towards the examined eye OEX, and transmitting the remaining 50% towards the other eye OV1 or OV2 to enable a sighting by both eyes. The dichroic separator BST3 then transmits all the light from the reference source SLD towards the examined eye OEX, at the same time taking advantage of a spectral difference between the reference source SLD (830 nm) and the target pattern MAM (800 nm). A 50/50 separator plate, which is spectrally totally neutral is also suitable, but 50% of the light from the SLD is then sent towards the eye which is not studied. A filter makes it possible to eliminate this image if it is judged harmful by the subject.

In order to be able to examine either eye, while simultaneously ensuring a sighting by both eyes, the system has a central examination location OEX, as well as two sighting locations OV1 and OV2, arranged on either side of this examination location OEX.

When the left eye is at the central location in order to be examined, the right eye receives the image of the target pattern MAM in its sighting location OV1 by the retractable return means, for example two mirrors MT1 and MT2. When it is the right eye which is at the location OEX, the return means may be retracted or cancelled and the image of the target pattern MAM reaches the left eye in its sighting location OV2.

As illustrated in FIG. 5, the system may also comprise, or collaborate with, means IRIS of monitoring movements of the eye to be examined, collaborating with the tomography device. This may be, for example, a camera with image recognition carrying out a monitoring or "tracking", for example of the retina or of the pupil or edges of the iris, in order to detect and evaluate the movements of the eye.

Knowledge of the movements of the eye can then be used by the system to adapt to displacements of the zone to be examined, for example by coordinating the adjustments and exposures with the different positions detected or envisaged for this zone to be examined, or by enabling a spatial and/or temporal optimisation of the adaptive optics. It is possible, for example, to take advantage of natural periods of stabilisation of the pupil or the retina in order to carry out all or some of the desired adjustments or measurements.

The image of the eye examined reaches the means IRIS of monitoring the eye by a separator BST2 inserted into the optical path, for example between the eye and the reference source SLD. Advantageously, for example, in order not to harm the subject, this separator BST2 is dichroic and the monitoring of the movements of the eye is carried out in non-visible light, for example, infrared.

The means of monitoring IRIS may comprise, for example, a device for measuring ocular movements, such as those developed by the Metrovision company.

The invention may in particular be used to produce or complement a device for retinal imaging, or for corneal topography, or for measuring a film of tears.

Of course, the invention is not limited to the examples which have just been described and numerous adjustments can be made to these examples without exceeding the framework of the invention.

The invention claimed is:

1. An in vivo tomography system with high axial and lateral resolution of the human retina, comprising:
   a Michelson interferometer, producing a full-field tomography setup by interference at coherence length (OCT) with a Z scanning,
   an input light source arranged in an input arm of the interferometer,
   adaptive optical means, designed to correct wavefronts originating from the eye and directed to the eye, comprising a reference source, a deformable mirror and means of analysing the wave surface,
   means of detection, arranged in an imaging arm of the interferometer, designed to produce an image from an interferometric measurement according to the OCT principle, and
   means of adjusting the focussing of the means of analysis of the wave surface,
      wherein the means of adjusting the focussing are arranged to force the deformable mirror to adopt an additional curvature, so as to conjugate the input light source and the means of detection with a point at a predetermined depth in the retina, said means of adjustment being controlled in synchronism with the Z scanning of the OCT tomography setup.

2. The system according to claim 1, characterized in that the adaptive optical means are arranged between the Michelson interferometer and the eye to be examined.

3. The system according to claim 1, further comprising means for controlling the adaptive optical means based on wavefront measurements made downstream of said adaptive optical means on a point image of the reference source produced on the retina of the eye.

4. The system according to claim 3, further including means for introducing an additional light beam, independent of the measurement beam, focussed on the retina.

5. The system according to claim 1, wherein the means of analysing the wave surface comprise an analyser of the Shack-Hartmann type.

6. The system according to claim 1, further including means for compensating for the effects of birefringence of the cornea, which are arranged in front of the eye.

7. The system according to claim 1, wherein rectilinearly polarized light passes through the two arms of the interferometer.

8. The system according to claim 7, further including a polarizing cube in order to obtain two mutually perpendicular polarizations in each arm.

9. The system according to claim 8, wherein the two arms of the interferometer comprise means for switching the polarization by 90 degrees between the outward and return legs.

10. The system according to claim 9, wherein the means for switching the polarization comprise a quarter-wave plate.

11. The system according to claim 7, wherein the interferometer is illuminated with linearly polarized light.

12. The system according to claim 7, further including means for adjusting the orientation of the input rectilinear polarization, so as to obtain a predetermined division of the fluxes injected into the two arms of the interferometer.

13. The system according to claim 6, wherein a quarter-wave plate is placed closest to the eye, before the birefringence compensation means.

14. The system according to claim 1, further including means of filtering the corneal reflection.

15. The system according to claim 14, wherein the means for filtering the corneal reflection comprise a field diaphragm arranged to diaphragm the essential component of the flux reflected by the cornea.

16. The system according to claim 1, further including means for tuning the adjustment to a given depth, through reaction of the adaptive optical means to an overall defocussing of the assembly constituted by the reference source and the analyser means.

17. The system according to claim 1, further including an active target pattern.

18. The system according to claim 1, further including means for freezing the shape of the adaptive optical means for the duration of an exposure.

19. The system according to claim 1, wherein the reference source is arranged upstream of the adaptive optical means.

20. The system according to claim 1, wherein the reference source is inserted into the optical path between the adaptive optical means and the eye to be examined.

21. The system according to claim 1, further including means for tracking the movement of the eye to be examined with the means of adjustment or detection.

22. The system according to claim 1, further including a measurement arm of the Michelson interferometer, wherein in said measurement arm there is means for compensating for the effects of the focal chromatism of the eye.

23. The system according to claim 1, further including a reference arm of the Michelson interferometer, wherein in said reference arm there is means of compensating for the dispersion of the path differences.

24. An in vivo tomography method with high axial and lateral resolution of the human retina, comprising:
   a full-field tomography by interference with low coherence length (OCT) with a Z scanning, using an input light source,
   a production of an image of the retina by means of detection, from an interferometric measurement according to the OCT principle,
   a correction of the wavefronts originating from the eye and reaching the eye, by adaptive optical means, arranged between the interferometer and the eye, said correction comprising an analysis operation of the wave surface on the retina, and
   an adjustment of the focussing of the wave surface analysis operation;
   wherein the focussing adjustment is carried out so as to conjugate the input light source and the means of detection with a point of predetermined depth in the retina, in synchronism with the Z scanning of the OCT tomography.

25. The method according to claim 24, wherein the interferometric measurement comprises a measurement of the contrast of the fringes without modulation by the method termed Wollaston.

26. The method according to claim 24, further including a compensation for the effects of birefringence of the cornea.

27. The method according to claim 26, further including a linear polarization of the reference source and a switching of the polarization between outward and return paths.

28. The method according to claim 24, further including a filtering of the corneal reflection.

29. The method according to claim 24, further including a tuning the adjustment to a given depth, by controlling the adaptive optical means in reaction to an overall defocussing of the assembly constituted by the reference source and the wave surface analyser means.

30. The method according to claim 24, further including an adjustment of the focussing of the wave surface analyser means.

31. The method according to claim 24, further including a freezing of the shape of the adaptive optical means for the duration of an exposure.

32. The method according to claim 24, further including a compensation for the effects of the focal chromatism of the eye.

33. The method according to claim 24, further including a compensation for the dispersion of the path differences.

34. The method according to claim 24, further including a command to the wavefront analyser obliging it to work in defocussed mode.

* * * * *